United States Patent
Luo et al.

(10) Patent No.: US 9,713,598 B2
(45) Date of Patent: Jul. 25, 2017

(54) TREATMENT OF INSULIN RESISTANCE ASSOCIATED WITH PROLONGED PHYSICAL INACTIVITY

(71) Applicant: ABBOTT LABORATORIES, Abbott Park, IL (US)

(72) Inventors: Menghua Luo, New Albany, OH (US); Suzette Pereira, Westerville, OH (US); Neile Edens, Austin, TX (US); Gerard Davis, Wauconda, IL (US); Susan Gawel, LaGrange Park, IL (US); Raj Chandran, Evanston, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/775,972

(22) PCT Filed: Mar. 14, 2014

(86) PCT No.: PCT/US2014/027524
§ 371 (c)(1),
(2) Date: Sep. 14, 2015

(87) PCT Pub. No.: WO2014/152606
PCT Pub. Date: Sep. 25, 2014

(65) Prior Publication Data
US 2016/0022617 A1 Jan. 28, 2016

Related U.S. Application Data

(60) Provisional application No. 61/783,301, filed on Mar. 14, 2013, provisional application No. 61/840,990, filed on Jun. 28, 2013, provisional application No. 61/866,061, filed on Aug. 15, 2013.

(51) Int. Cl.
*A61K 31/19* (2006.01)
*G01N 33/68* (2006.01)

(52) U.S. Cl.
CPC ......... *A61K 31/19* (2013.01); *G01N 33/6893* (2013.01); *G01N 2333/47* (2013.01); *G01N 2333/4704* (2013.01); *G01N 2333/575* (2013.01); *G01N 2800/52* (2013.01)

(58) Field of Classification Search
CPC ............... A61K 31/19; G01N 33/6893; G01N 2333/4704; G01N 2800/52; G01N 2333/47; G01N 2333/575
See application file for complete search history.

(56) References Cited

U.S. PATENT DOCUMENTS

| | | | |
|---|---|---|---|
| 7,601,370 B2 | 10/2009 | Johnson | |
| 8,217,077 B2 | 7/2012 | Baxter et al. | |
| 2006/0003959 A1 | 1/2006 | Burden et al. | |
| 2007/0093553 A1 | 4/2007 | Baxter et al. | |
| 2008/0171319 A1 | 7/2008 | Urdea et al. | |
| 2012/0053240 A1 | 3/2012 | Rathmacher et al. | |
| 2012/0178811 A1 | 7/2012 | Thomas et al. | |
| 2012/0189717 A1 | 7/2012 | Baxter et al. | |
| 2012/0195873 A1 | 8/2012 | Miller et al. | |
| 2012/0196829 A1 | 8/2012 | Baxter et al. | |
| 2012/0231482 A1 | 9/2012 | Murray et al. | |

FOREIGN PATENT DOCUMENTS

| | | | |
|---|---|---|---|
| WO | 2011098449 A1 | 8/2011 | |
| WO | 2012092035 A1 | 7/2012 | |
| WO | WO 2012092035 A1 * | 7/2012 | ............ A61K 31/19 |
| WO | 2013142424 A1 | 9/2013 | |

OTHER PUBLICATIONS

Newgard et al (Cell Metabolism, Apr. 8, 2009, 9, 311-326).*
International Search Report and Written Opinion for PCT/US2014/027524 dated Dec. 1, 2014.
International Preliminary Report on Patentability for PCT/US2014/027524 dated Sep. 15, 2015.
Communication Pursuant to Rules 161(1) and 162 for EP 14719475.7 dated Oct. 23, 2015.
Office Action in Vietnam Patent Application No. 1-2015-03826 dated Nov. 12, 2015.
Abbott Nutrition, "HMB (beta-hydroxy-beta-methylbutyrate): A Scientific Review," http://abbottnutrition.com/downloads/resourcecenter/hmb-a-scientific-review.pdf (Apr. 1, 2010).
Au et al., "Increased connective tissue growth factor associated with cardiac fibrosis in the mdx mouse model of dystrophic cardiomyopathy," Int. J. Exp. Path. (2011), vol. 92, 57-65.
Aversa et al., "β-hydroxy-β-methylbutyrate (HMB) attenuates muscle and body weight loss in experimental cancer cachexia," Intl J Oncology (2011), vol. 38, 713-720.
Clements et al., "Nutritional effect of oral supplement enriched in beta-hydroxybeta-methylbutyrate, glutamine and arginine on resting metabolic rate after laparoscopic gastric bypass," NIH-PA Author Manuscript, Oct. 24, 2011.
Esteghamati et al., "Association between physical activity and insulin resistance in Iranian adults: National Surveillance of Risk Factors of Non-Communicable Diseases (SuRFNCD-2007)," Preventive Medicine (2009), vol. 49, 402-406.
Fiotti et al., "Body composition and muscular strength changes after moderate activity: association with matrix metalloproteinase polymorphisms," Arch Gerontol Geriatr (2009), vol. 49, Suppl 1, 83-94, Abstract Only.

(Continued)

*Primary Examiner* — Sudhakar Katakam
(74) *Attorney, Agent, or Firm* — Porter Wright Morris & Arthur LLP

(57) ABSTRACT

Insulin resistance biomarkers and related methods of using the biomarkers are provided. The biomarkers may be blood biomarkers and include C-peptide, Insulin-Like Growth Factor-Binding Protein 2 (IGFBP-2), and Leptin. Also provided is a method of reducing the effect of prolonged physical inactivity on insulin resistance in a subject who is experiencing prolonged physical inactivity, or who is expected to experience prolonged physical inactivity in the near future.

15 Claims, No Drawings

(56) References Cited

OTHER PUBLICATIONS

Gerlinger-Romero et al., "Chronic supplementation of beta-hydroxy-beta methylbutyrate (HMB) increases the activity of the GH/IGF-I axis and induces hyperinsulinemia in rats," Growth Hormone & IGF Research (2011), vol. 21, 57-62.

Hamburg et al., "Physical Inactivity Rapidly Induces Insulin Resistance and Microvascular Dysfunction in Healthy Volunteers," Arterioscler Thromb Vasc Biol (2007), vol. 27, 2650-2656.

Hao et al., "β-Hydroxy-β-methylbutyrate reduces myonuclear apoptosis during recoveryfrom hind limb suspension-induced muscle fiber atrophy in aged rats," Am. J. Physiol. Regul Integr Comp Physiol (2011), vol. 301, R701-R715.

Hsieh et al., "Anti-inflammatory and anticatabolic effects of shorf-ferm b-hydroxy-b-methylbutyrate supplementation on chronic obstructive pulmonary disease patients in intensive care unit," Asia Pac J Clin Nutr (2006), vol. 15, No. 14, 544-550.

Hsieh et al., "Effect of β-hydroxy-β-methylbutyrate on protein metabolism in bed-ridden elderly receiving tube feeding," Asia Pac J Clin Nutr (2010), vol. 19, No. 2, 200-208.

Manicourt et al., "Serum Levels of Hyaluronan, Antigenic Keratan Sulfate, Matrix Metalloproteinase 3, and Tissue Inhibitor of Metalloproteinases 1 Change Predictably in Rheumatoid Arthritis Patients Who Have Begun Activity After a Night of Bed Rest," Arthritis & Rheumatism (1999), vol. 42, No. 9, 1861-1869.

Rai et al., "Bone mineral density, bone mineral content, gingival crevicular fluid (matrix metalloproteinases, cathepsin K, osteocalcin), and salivary and serum osteocalcin levels in human mandible and alveolar bone under conditions of simulated microgravity," J Oral Sci (2010), vol. 52, No. 3, 385-390.

Reznick et al., "Expression of matrix metalloproteinases, inhibitor, and acid phosphatasein muscles of immobilized hindlimbs of rats," Muscle Nerve (2003), vol. 27, No. 1, 51-59, Abstract Only.

Seene et al., "Review on aging, unloading and reloading: changes in skeletal muscle quantity and quality," Arch Gerontol Geriatr (2012), vol. 54, No. 2, 374-380, Abstract Only.

* cited by examiner

TREATMENT OF INSULIN RESISTANCE ASSOCIATED WITH PROLONGED PHYSICAL INACTIVITY

CROSS REFERENCE TO RELATED APPLICATIONS

This application is the U.S. national stage entry of International Application No. PCT/US2014/027524, filed Mar. 14, 2014, which claims priority to and the benefit of U.S. Provisional Application No. 61/783,301, filed Mar. 14, 2013, U.S. Provisional Application No. 61/840,990, filed Jun. 28, 2013, and U.S. Provisional Application No. 61/866,061, filed Aug. 15, 2013, the entire contents of which are incorporated herein by reference.

FIELD

The present disclosure relates to biomarkers. More particularly, the present disclosure relates to insulin resistance biomarkers whose levels in blood change during prolonged or extended periods of physical inactivity and methods of using these biomarkers. The present disclosure also relates to methods of reducing or attenuating the insulin resistance associated with a prolonged period of physical inactivity in human subjects.

BACKGROUND

In various scenarios adults are required to undergo extended bed rest. For example, adults who are hospitalized due to illness, injury or surgery may be required to stay in bed for extended periods of time. Similarly, adults who are in a rehabilitation center or at home may be bedridden or physically inactive over an extended period of time.

Extended bed rest has been shown to decrease whole body and muscle insulin sensitivity (Alibegovic, A. C. et al., *Diabetes* 58: 2749-2756, 2009), to diminish blood glucose control, and to impair glucose tolerance (Mikines, K. J. et al., *Am J Physiol* 257: E43-48, 1989). These adverse metabolic changes can lead to poor quality of life outcomes.

SUMMARY

Provided herein are methods of reducing or lessening the effect of prolonged physical inactivity on insulin resistance in a human subject. The method comprises administering a therapeutically effective amount of β-hydroxy-β-methylbutyrate (HMB) to a subject who is experiencing prolonged physical inactivity or is expected to experience prolonged physical inactivity in the near future. In certain embodiments, HMB is administered to the subject in an amount, manner, and for a time sufficient to lessen the increase or decrease in circulating levels of C-peptide, Insulin-Like Growth Factor-Binding Protein 2 (IGFBP-2), and/or Leptin that occurs with prolonged physical inactivity in untreated control subjects. In one embodiment, HMB is administered in an amount, manner, and for a time sufficient to reduce the increase in C-peptide that occurs with prolonged physical inactivity in untreated control subjects. In another embodiment, HMB is administered in an amount, manner, and for a time sufficient to reduce the increase in circulating Leptin that occurs with prolonged physical inactivity in untreated control subjects. In another embodiment, HMB is administered in an amount, manner, and for time sufficient to attenuate the decrease in circulating IGFBP-2 that occurs with prolonged physical inactivity in untreated control subjects. In another embodiment, HMB is administered in an amount, manner, and for a time sufficient to keep the levels of C-peptide and/or IGFBP-2 in a biological sample taken from the subject 3 or more days after the subject has become physically inactive comparable to the baseline levels of C-peptide and/or IGFBP-2.

Also provided are methods of evaluating the efficacy of an intervention on the insulin resistance associated with prolonged physical inactivity in a subject. In one embodiment, the method comprises: (a) measuring levels of one or more biomarkers selected from the group consisting of IGFBP-2, Leptin, and C-peptide in a biological sample taken from the subject prior to or on the day the subject becomes physically inactive; (b) administering an intervention to the subject, wherein the intervention is first administered to the subject before or on the day the subject becomes physically inactive; (c) measuring levels of said one or more biomarkers in a biological sample taken from the subject 3 days or more days after the subject becomes physically inactive; (d) calculating the difference between the levels measured in steps (a) and (c) for each of said one or more biomarkers; (e) comparing the one or more differences calculated in (d) to one or more control values based on the differences in the levels of said one or more biomarkers in comparable biological samples taken from untreated control subjects at comparable time points; and (f) characterizing the intervention as being efficacious if the one or more differences calculated in (d) are smaller than the control values for said one or more biomarkers.

In another embodiment, a method of evaluating the efficacy of an intervention on the insulin resistance associated with prolonged physical inactivity in a subject comprises: (a) administering an intervention to the subject, wherein the intervention is first administered to the subject before or on the day the subject becomes physically inactive; (b) measuring levels of one or more biomarkers selected from C-peptide and IGFBP-2 in a biological sample taken from the subject at 3 days or more after the subject becomes physically inactive; (c) comparing the levels measured in (b) to one or more baseline levels for the one or more biomarkers; and (d) characterizing the intervention as being efficacious if the measured levels of said one or more biomarkers are comparable to the baseline levels for said one or more biomarkers, respectively.

Also provided are systems for determining the efficacy of an intervention on the insulin resistance associated with prolonged physical inactivity in a subject. In one embodiment, the system comprises: (a) a sub-system for identifying a subject undergoing physical inactivity or expected to undergo physical inactivity in the near future; (b) a sub-system for taking a biological sample from the subject identified in (a) before or on the day the subject becomes physically inactive; (c) a sub-system for administering the intervention to the subject; (d) a sub-system for taking a biological sample from the subject identified in (a) at 3 or more days after the subject becomes physically inactive; and (e) a sub-system for measuring the levels of one or more biomarkers selected from C-Peptide, IGFBP-2, and Leptin in the biological samples obtained using sub-systems (b) and (d); and (f) a sub-system for calculating the difference in the levels of the one or more biomarkers in the biological samples obtained using sub-systems (b) and (d). In certain embodiments the system further comprises a sub-system for the comparing the one or more differences calculated by the sub-system of (f) to one or more control value based on the difference in the levels of the one or more biomarkers in comparable biological samples taken from untreated control subjects over a comparable period of time.

In one exemplary embodiment, a composition for use in the treatment of insulin resistance in a subject who is experiencing or is expected to experience prolonged physical inactivity in the near future is provided. The composition comprises β-hydroxy-β-methylbutyric acid (HMB) or a salt thereof.

DETAILED DESCRIPTION

The present invention will now be described by reference to more detailed embodiments. This invention may, however, be embodied in different forms and should not be construed as limited to the embodiments set forth herein. Rather these embodiments are provided so that this disclosure will be thorough and complete, and will convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

All publications, patent applications, patents, and other references mentioned herein are incorporated by reference in their entirety.

The present methods are based, at least in part, on inventors' discovery that levels of 3 circulating insulin resistance biomarkers change, i.e., increase or decrease, by statistically significant amounts in 18 healthy elderly subjects undergoing 10 days of bed rest. The methods are also based, at least in part, on inventors' discovery that intervention with HMB alters the changes in levels of 3 circulating biomarkers associated with insulin resistance.

Therapeutic Methods and Compositions

Provided herein is a method of attenuating or reducing the effect of prolonged inactivity on insulin resistance in a subject. In one embodiment, the method comprises administering a therapeutically effective amount of HMB to a human subject who is experiencing a prolonged period of physical inactivity or who is expected to experience a prolonged period of physical inactivity in the near future, i.e., within the next few days, the next few weeks or the next few months. For example, the subject may be scheduled to undergo a procedure (e.g., surgery) that may lead to a prolonged period of physical inactivity within the next 1, 2, 3, 4, 5, 6, etc. months. As used herein the term a "prolonged period of inactivity" refers to a period of inactivity that lasts 3 days or more. As used herein the term "physical inactivity" refers to a condition or situation in which the subject seldom moves his or her limbs or body. In certain embodiments, the present methods and systems are used on a subject experiencing hospitalization. The present methods and systems may be used on a subject whose activities are restricted by others, e.g., a subject who is restricted to bed rest by a physician or other health care provider. The present methods and systems may be used on a subject whose activities are limited due to surgery, injury, infirmity, frailty, old age, etc. The present methods and systems may be used on a subject whose physical inactivity is self-imposed, e.g. the subject is depressed.

Also provided herein is a composition for use in the treatment of insulin resistance in a subject who is experiencing or is expected to experience prolonged physical inactivity in the near future is provided. The composition comprises HMB or a salt thereof. In certain embodiments, the subject is experiencing hospitalization. In certain embodiments, the subject's activities are restricted by others, e.g., a subject who is restricted to bed rest by a physician or other health care provider. In certain embodiments, the subject is experiencing prolonged physical inactivity due to surgery, injury, infirmity, frailty, old age, etc. The present methods and systems may be used on a subject whose physical inactivity is self-imposed, e.g., the subject is depressed.

As used herein, the term "therapeutically effective amount" shall be understood as referring to the amount of HMB which provides any therapeutic benefit in the prevention, treatment, or management of at least one of the symptoms, complications or conditions associated with insulin resistance. In certain embodiments, HMB is first administered to the subject before physical inactivity commences. In certain embodiments, HMB is first administered when the subject becomes physically inactive, i.e., on the day the subject becomes physically inactive or within a day or two after the subject becomes physically inactive. In certain embodiments HMB is administered to the subject throughout the entire period of physical inactivity. In certain embodiments HMB is administered to the subject before and throughout part or all of the period of physical inactivity. In certain embodiments HMB is administered to the subject after the period of physical inactivity has ended. In certain embodiments HMB is administered to the subject up to one year. In certain embodiments HMB is administered to the subject for more than one year.

In certain embodiments the subject is an adult human subject, i.e., a subject 20 years of age or older. In certain embodiments the subject is an elderly human subject, i.e., a human subject 50 years of age or older.

In certain embodiments the HMB is administered in an amount, manner, and for a time sufficient to lessen the increase or decrease in circulating levels of C-peptide, IGFBP-2, and Leptin that occurs with prolonged physical inactivity in untreated control subjects. In one embodiment, HMB is administered in an amount, manner, and for a time sufficient to reduce the increase in circulating C-peptide levels that occurs with prolonged physical inactivity in untreated control subjects. In another embodiment, HMB is administered in an amount, manner, and for a time sufficient to reduce the increase in circulating Leptin levels that occurs with prolonged physical inactivity in untreated control subjects. In another embodiment, HMB is administered in an amount, manner, and for a time sufficient to attenuate the decrease in circulating IGFBP-2 levels that occurs with prolonged physical inactivity in untreated control subjects. In another embodiment, HMB is administered in an amount, manner and for a time sufficient to keep the levels of C-peptide and/or IGFBP-2 in biological samples taken from the subject at 3 or more days of physical inactivity comparable to baseline levels of C-peptide and/or IGFBP-2 in a biological sample taken from the subject at the beginning of or prior to the period of physical inactivity. As used herein the levels of the biomarker in the two biological samples are "comparable" if they differ by 20% or less.

HMB

The term HMB, which is also referred to as β-hydroxy-β-methylbutyric acid, or β-hydroxy-isovaleric acid, can be represented in its free acid form as $(CH_3)_2(OH)CCH_2COOH$. HMB is a metabolite of leucine formed by transamination to α-ketoisocaproate (KIC) in muscle followed by oxidation of the KIC in the cytosol of the liver to give HMB. While any suitable form of HMB can be used within the context of the present invention, preferably, HMB is selected from the group consisting of a free acid, a salt, an ester, and a lactone; more preferably, HMB is in the form of a non-toxic, edible salt. Preferably, the HMB salt is water-soluble or becomes water-soluble in the stomach or intestines of a patient. More preferably, the HMB salt is selected from the group consisting of a sodium salt, a potassium salt, a magnesium salt, a chromium salt, and a calcium salt. However, other non-toxic salts, such as other alkali metal or alkaline earth metal salts, can be used.

Similarly, any pharmaceutically acceptable ester can be used in the context of the present invention. Desirably, the HMB ester is rapidly converted to HMB in its free acid form. Preferably, the HMB ester is a methyl ester or ethyl ester. HMB methyl ester and HMB ethyl ester are rapidly converted to the free acid form of HMB. Likewise, any pharmaceutically acceptable lactone can be used in the context of the present invention. Desirably, the HMB lactone is rapidly converted to HMB in its free acid form. Preferably, the HMB lactone is an isovalaryl lactone or a similar lactone. Such lactones are rapidly converted to the free acid form of HMB.

Methods for producing HMB and its derivatives are well known in the art. For example, HMB can be synthesized by oxidation of diacetone alcohol. One suitable procedure is described by Coffman et al., *J. Am. Chem. Soc.* 80: 2882-2887 (1958). As described therein, HMB is synthesized by an alkaline sodium hypochlorite oxidation of diacetone alcohol. The product is recovered in free acid form, which can be converted to the desired salt. For example, 3-hydroxy-3-methylbutyric acid (HMBA) can be synthesized from diacetone alcohol (4-hydroxy-4-methylpentan-2-one) via oxidation using cold, aqueous hypochlorite (bleach). After acidifying the reaction mixture using HCl, the HMBA product is recovered by extraction using ethyl acetate, and separating and retaining the organic layer from the extraction mixture. The ethyl acetate is removed by evaporation and the residue dissolved in ethanol. After addition of $Ca(OH)_2$ and cooling, crystalline CaHMB can be recovered by filtration, the crystals washed with ethanol and then dried. Alternatively, the calcium salt of HMB is commercially available from Technical Sourcing International (TSI) of Salt Lake City, Utah.

The routes for administering HMB include an oral diet, tube feeding and peripheral or total parenteral nutrition. The preferred embodiment for the present methods is by the oral route. An alternate to oral feeding is tube feeding by means of nasogastric, nasoduodenal, esophagostomy, gastrostomy, or jejunostomy tubes.

If desired, the HMB may be administered alone, without a carrier. The HMB may simply be dissolved in water and consumed by the patient. Alternatively, the HMB may be sprinkled on food, dissolved in coffee, etc. The total daily dose for the patient will vary widely, but typically a patient will benefit from consuming at least 2 g/day of HMB. Alternatively, the total daily dose may be from 20 to 40 mg/kg body weight/day.

In a further embodiment, the HMB may be incorporated into pills, capsules, rapidly dissolved tablets, lozenges, etc. The active dose can vary widely, but will typically range from 250 mg to 1 g/dose with the patient consuming from 2 to 8 doses/day to achieve the target of 2 g/day minimum. Methods for preparing such dosage forms are well known in the art. The reader's attention is directed to the most recent edition of Remingtons Pharmaceutical Sciences for guidance on how to prepare such dosage forms.

In a further embodiment, the HMB may be combined with other nutritional supplements such as amino acids. One example of such supplement is Juven®, a powder (sachet) containing 1.5 grams HMB, 5 grams arginine, and 5 grams glutamine.

Nutritional Matrices

While the HMB may be administered as a single entity, it will typically be incorporated into food products and consumed by the patient during their meals or snack. If desired, the patient may simply modify the recipe of foods they normally consume by sprinkling on food, dissolving in coffee, etc.

In a further embodiment, the HMB will be incorporated into beverages, bars, cookies, etc. that have been specifically designed to enhance the palatability of the HMB and increase the selection of alternative forms, thereby enhancing patient/consumer acceptance.

Typically, the HMB will be incorporated into meal replacement beverages. The HMB may also be incorporated into meal replacement bars. Alternatively, the HMB may be incorporated into juices, carbonated beverages, bottled water, etc. Additionally, the HMB may be incorporated into medical nutritionals designed to support specific disease states. Methods for producing any of such food products are well known to those skilled in the art. The following discussion is intended to illustrate such food products and their preparation.

Most meal replacement products (e.g., bars or liquids) provide calories from fat, carbohydrates, and protein. These products also typically contain vitamins and minerals, because they are intended to be suitable for use as the sole source of nutrition. While these meal replacement products may serve as the sole source of nutrition, they typically don't. Individuals consume these products to replace one or two meals a day, or to provide a healthy snack. The nutritional products of this invention should be construed to include any of these embodiments.

The meal replacements will contain suitable carbohydrates, lipids and proteins as is known to those skilled in the art of making nutritional formulas. Suitable carbohydrates include, but are not limited to, hydrolyzed, intact, naturally and/or chemically modified starches sourced from corn, tapioca, rice or potato in waxy or non waxy forms; and sugars such as glucose, fructose, lactose, sucrose, maltose, high fructose corn syrup, corn syrup solids, fructooligosaccharides, and mixtures thereof.

Suitable protein sources include, but are not limited to, milk, whey and whey fractions, soy, rice, meat (e.g., beef), animal and vegetable (e.g., pea, potato), egg (egg albumin), gelatin and fish. Suitable intact protein sources include, but are not limited to, soy based, milk based, casein protein, whey protein, rice protein, beef collagen, pea protein, potato protein, and mixtures thereof.

Optionally, the intact protein source is enriched in large neutral amino acids (LNAA) comprising valine, isoleucine, leucine, threonine, tyrosine and phenylalanine Typically, about 40% of casein, whey and soy protein sources are large neutral amino acids. For example, caseinate contains about 38 wt/wt % LNAA, whey protein concentrate contains about 39 wt/wt % LNAA and soy protein isolate contains about 34 wt/wt % LNAA. Typically, the meal replacement is formulated with a protein source that will deliver about 1 to 25 grams of LNAA per day, preferably from about 1 to 20 gram of LNAA per day, more preferably from about 4 to 20 grams of LNAA per day. As an example, a meal replacement consumed 3 times a day that contains a protein comprising 4.8 grams LNAA will deliver 14.4 grams LNAA per day.

The meal replacements preferably also contain vitamins and minerals in an amount designed to supply or supplement the daily nutritional requirements of the person receiving the formula. Those skilled in the art recognize that nutritional formulas often include overages of certain vitamins and minerals to ensure that they meet targeted level over the shelf life of the product. These same individuals also recognize that certain micro ingredients may have potential benefits for people depending upon any underlying illness or disease that the patient is afflicted with. For example, cancer patients benefit from such antioxidants as beta-carotene, vitamin E, vitamin C and selenium. The food products preferably include, but are not limited to, the following vitamins and minerals: calcium, phosphorus, sodium, chloride, magnesium, manganese, iron, copper, zinc, selenium, iodine, chromium, molybdenum, conditionally essential nutrients m-inositol, carnitine and taurine, and Vitamins A, C, D, E, K and the B complex, and mixtures thereof.

In addition to fiber, the meal replacements may also contain oligosaccharides such as fructooligosaccharides (FOS) or glucooligosaccharides (GOS). Oligosaccharides are rapidly and extensively fermented to short chain fatty acids by anaerobic microorganisms that inhabit the large bowel. These oligosaccharides are preferential energy sources for most Bifidobacterium species, but are not utilized by potentially pathogenic organisms such as *Clostridium perfingens, C. difficile*, or *Eschericia coli*.

Typically, the FOS comprises from 0 to 5 g/serving of the meal replacement, preferably from 1 to 5 g/serving, more preferably from 2 to 4 g/serving of the meal replacement.

The meal replacements may also contain a flavor to enhance its palatability. Artificial sweeteners may be added to complement the flavor and mask salty taste. Useful artificial sweeteners include saccharin, nutrasweet, sucralose, acesulfane-K (ace-K), etc. Meal replacements can be manufactured using techniques well known to those skilled in the art.

Solid compositions such as bars, cookies, etc. may also be manufactured utilizing techniques known to those skilled in the art. For example, they may be manufactured using cold extrusion technology as is known in the art. To prepare such compositions, typically all of the powdered components will be dry blended together. Such constituents typically include the proteins, vitamin premixes, certain carbohydrates, etc. The fat-soluble components are then blended together and mixed with the powdered premix above. Finally any liquid components are then mixed into the composition, forming a plastic like composition or dough.

The process above is intended to give a plastic mass that can then be shaped, without further physical or chemical changes occurring, by the procedure known as cold forming or extrusion. In this process, the plastic mass is forced at relatively low pressure through a die, which confers the desired shape. The resultant extrudate is then cut off at an appropriate position to give products of the desired weight. If desired the solid product is then coated, to enhance palatability, and packaged for distribution.

The solid compositions of the instant invention may also be manufactured through a baked application or heated extrusion to produce cereals, cookies, and crackers. One knowledgeable in the arts would be able to select one of the many manufacturing process.

As noted above, the HMB may also be incorporated into juices, non-carbonated beverages, carbonated beverages, electrolyte solutions, flavored waters (hereinafter collectively "beverage"), etc. The HMB will typically comprise from 0.5 to 2 g/serving of the beverages. Methods for producing such beverages are well known in the art. The reader's attention is directed to U.S. Pat. Nos. 6,176,980 and 5,792,502, the contents of each which are hereby incorporated by reference. For example, all of the ingredients, including the HMB are dissolved in an appropriate volume of water. Flavors, colors, vitamins, etc. are then optionally added. The mixture is then pasteurized, packaged and stored until shipment.

In some embodiments, the nutritional products that contain HMB, such as Ensure Clear®, lack fat.

Dosing

The amount of HMB that is sufficient to reduce insulin resistance associated with prolonged physical inactivity in a human subject can be determined in clinical studies that employ a population of control subjects. The dosing can also be optimized to the subject undergoing a prolonged period of physical inactivity. In certain embodiments, the dosing is optimized to the subject undergoing a prolonged period of physical inactivity by monitoring the circulating levels of the biomarkers over the course of the period of physical inactivity and evaluating the efficacy of the HMB intervention as described below.

In some cases, when the composition is orally administered about twice a day for a minimum of two weeks; the dose is sufficient to provide at least about 2 grams of HMB per day; for example, between 1 and 10 grams per day for a typical 70 kg person, more ideally between about 2 and 5 grams per day. The dosing on a body weight basis may range from about 0.01 to about 0.10 grams per kg body weight, more ideally between 0.02 and 0.07 grams per kg body weight.

Evaluation Methods

Also provided are methods and systems for evaluating the efficacy of an intervention on insulin resistance associated with prolonged physical inactivity, e.g., bed rest, immobilization, etc. In one embodiment, the method comprises: (a) measuring the levels of one or more biomarkers selected from IGFBP-2, Leptin and C-peptide in a biological sample taken from a subject before or on the day the subject becomes physically inactive; (b) administering the intervention to the subject, wherein the intervention is first administered to the subject prior to or at the beginning of the period of physical inactivity; (c) measuring the levels of the one or more biomarkers measured in step (a) in a biological sample obtained from the subject at 3 or more days after the subject becomes physically inactive; (d) calculating the difference between the levels of the one or more biomarkers measured in (a) and the levels of the one or more biomarkers measured in (c); (e) comparing the one or more differences calculated in (d) to one or more control values based on the difference in the levels of the one or more biomarkers in comparable biological samples obtained from untreated control subjects at comparable time points; and (f) characterizing the intervention as being efficacious if the one or more differences calculated in (d) are smaller than the one or more control values.

In certain embodiments, the method employs C-peptide as one of the one or more biomarkers. As shown in Table 1 below, circulating levels of C-peptide increase in untreated control subjects who have experienced 10 days of bed rest. Interventions that reduce this increase by a statistically significant amount are characterized as being efficacious.

In certain embodiments, the method employs Leptin as one of the one or more biomarkers. As shown in Table 1 below, circulating levels of Leptin increase in untreated control subjects who have experienced 10 days of bed rest. Interventions that reduce this increase by a statistically significant amount are characterized as being efficacious.

In certain embodiments, the method employs IGFBP-2 as one of the one or more biomarkers. As shown in Table 1 below, circulating levels of IGFBP-2 decrease in untreated control subjects who have experienced 10 days of bed rest. Interventions that attenuate this decrease by a statistically significant amount are characterized as being efficacious.

In certain embodiments, the intervention is first administered to the subject at the beginning of the period of physical inactivity, i.e., on the day the period of physical inactivity begins. In other embodiments, the intervention is first administered to the subject before the period of physical inactivity begins, e.g., 1 or 2 days or weeks before the period of physical inactivity begins. In certain embodiments, the intervention is administered continuously throughout the testing period. In certain embodiments, the intervention is administered to the subject throughout the entire period of physical inactivity and after the period of physical inactivity ends. Thus, the period of time that the intervention is administered to the subject may be longer than the period of physical inactivity.

The first biological sample is used to determine baseline values for the one or more biomarkers. Thus, the first biological sample may be taken from the subject prior to or at the beginning of the period of physical inactivity. A first comparative biological sample is taken from the subject at 3 or more days after the period of physical inactivity has commenced and at 3 or more days after intervention has started. In certain embodiments a comparative biological sample is taken from the subject 10 or more days after the period of inactivity has commenced. In certain embodiments a comparative biological sample is obtained from the subject 3-7 days after the period of inactivity has commenced. In certain embodiments a comparative biological sample is obtained from the subject 1-4 weeks after the period of inactivity has commenced and/or after the intervention has begun. In certain embodiments a comparative biological sample is obtained from the subject 1-3 months after the period of inactivity has commenced. In certain embodiments, more than one comparative sample is taken from the subject.

In another embodiment, a method of evaluating the efficacy of an intervention on insulin resistance associated with prolonged physical inactivity comprises: (a) administering the intervention to the subject, wherein the intervention is first administered to the subject prior to or at the beginning of physical inactivity; (b) measuring levels of one or more biomarkers selected from C-peptide and IGFBP-2 in a biological sample taken from the subject at 3 or more days after physical inactivity begins; (c) comparing the levels measured in (b) to one or more baseline levels of said one or more biomarkers in a biological sample obtained from the subject prior to or at the beginning of the period of physical inactivity; and (d) characterizing the intervention as being efficacious if the levels of said one or more biomarkers measured in step (b) are comparable to the one or more baseline levels for said one or more biomarkers. As described herein, the levels are comparable if the difference between the baseline levels of the biomarker and the levels measured in step (b) is 20% or less.

Biological Samples

Biological samples suitable for use in the present methods include, but are not limited, to whole blood samples, samples of blood fractions, including but not limited to serum and plasma. The sample may be fresh blood or stored blood (e.g. in a blood bank) or blood fractions. The sample may be a blood sample expressly obtained for the assays of this invention or a blood sample obtained for another purpose which can be subsampled for the assays of this invention.

In one embodiment, the blood sample is whole blood. Whole blood may be obtained from the subject using standard clinical procedures. In another embodiment, the blood sample is plasma. Plasma may be obtained from whole blood samples by centrifugation of anti-coagulated blood. Such process provides a buffy coat of white cell components and a supernatant of the plasma. In another embodiment, the blood sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC). Any of a number of standard aqueous buffer solutions, employing one of a variety of buffers, such as phosphate, Tris, or the like, at physiological pH can be used.

Other biological samples that may be used in the present methods include, but are not limited to, urine and saliva.

Measuring Levels of the Biomarkers

Levels of each of the biomarkers in the subject's blood samples can be determined by various methods such as by using polyclonal or monoclonal antibodies that are immunoreactive with the respective biomarker or by using other binding agents such as aptamers or protein domains suitable for binding target from phase display libraries. For example, antibodies immunospecific for IGFBP-2 may be made and labeled using standard procedures and then employed in immunoassays to detect the presence of IGFBP-2 in the sample. Suitable immunoassays include, by way of example, radioimmunoassays, both solid and liquid phase, fluorescence-linked assays, competitive immunoassays, or enzyme-linked immunosorbent assays. In certain embodiments, the immunoassays are also used to quantify the amount of the biomarker that is present in the sample.

Each of the biomarkers can be used as an immunogen to produce antibodies immunospecific for the oxidized protein or peptide fragment. The term "immunospecific" means the antibodies have substantially greater affinity for the immunogen than for other proteins. Such antibodies may include, but are not limited to, polyclonal, monoclonal, chimeric, single chain, and Fab fragments.

Antibodies raised against the select biomarker species are produced according to established procedures. Generally, the biomarker is used to immunize a host animal. Suitable host animals, include, but are not limited to, rabbits, mice, rats, goats, and guinea pigs. Various adjuvants may be used to increase the immunological response in the host animal. The adjuvant used depends, at least in part, on the host species. Such animals produce heterogenous populations of antibody molecules, which are referred to as polyclonal antibodies and which may be derived from the sera of the immunized animals.

Polyclonal antibodies are generated using conventional techniques by administering the biomarker to a host animal. Depending on the host species, various adjuvants may be used to increase immunological response. Among adjuvants used in humans, Bacilli-Calmette-Guerin (BCG), and *Corynebacterium parvum* are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols that involve competitive binding or immunoradiometric assays and typically involve the measurement of complex formation between the respective biomarker and the antibody.

The present antibodies may be used to detect the presence of or measure the amount biomarker in a biological sample from the subject. The method comprises contacting a sample taken from the individual with one or more of the present antibodies; and assaying for the formation of a complex between the antibody and the biomarker in the sample. For ease of detection, the antibody can be attached to a substrate such as a column, plastic dish, matrix, or membrane, preferably nitrocellulose. In certain embodiments, the method employs an enzyme-linked immunosorbent assay (ELISA) or a Western immunoblot procedure.

The presence or amount of one or more biomarkers can be determined using antibodies that specifically bind to each marker as well as any additional biomarkers if such additional biomarkers are used. Examples of antibodies that can be used include a polyclonal antibody, a monoclonal antibody, a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a Fab', a bispecific antibody, a F(ab')2, a Fv and combinations thereof. For example, the immunological method may include (a) measuring the levels of a biomarker by: (i) contacting the test sample with at least one capture antibody, wherein the capture antibody binds to an epitope on the biomarker or a fragment thereof to form a capture antibody-antigen complex; (ii) contacting the capture antibody-antigen complex with at least one detection antibody comprising a detectable label, wherein the detection antibody binds to an epitope on the biomarker (antigen) that is not bound by the capture antibody and forms a capture antibody-antigen-detection antibody complex; and (iii) determining the biomarker level in the test sample based on the signal generated by the detectable label in the capture antibody- antigen-detection antibody complex formed in (a)(ii). Any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA. Specific immunological binding of the antibody to the marker can be detected via direct labels, such as fluorescent or luminescent tags, metals and radionuclides attached to the antibody or via indirect labels, such as alkaline phosphatase or horseradish peroxidase.

The use of immobilized antibodies or fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and then processed quickly through washes and detection steps to generate a measurable signal, such as a colored spot.

The sandwich ELISA measures the amount of antigen between two layers of antibodies (i.e. a capture antibody and a detection antibody (which may be labeled with a detectable label)). The marker to be measured may contain at least two antigenic sites capable of binding to antibody. Either monoclonal or polyclonal antibodies may be used as the capture and detection antibodies in the sandwich ELISA.

Generally, at least two antibodies are employed to separate and quantify the marker of interest (as well as any additional biomarkers), in a test or biological sample. More specifically, the at least two antibodies bind to certain epitopes of the marker forming an immune complex which is referred to as a "sandwich". One or more antibodies can be used to capture the marker in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, both antibodies binding to their epitope may not be diminished by the binding of any other antibody in the assay to its respective epitope. In other words, antibodies may be selected so that the one or more first antibodies brought into contact with a test sample suspected of containing the marker do not bind to all or part of an epitope recognized by the second or subsequent antibodies, thereby interfering with the ability of the one or more second detection antibodies to bind to the marker.

In a preferred embodiment, a test or biological sample suspected of containing the marker can be contacted with at least one first capture antibody (or antibodies) and at least one second detection antibody, either simultaneously or sequentially. In the sandwich assay format, a test sample suspected of containing the marker is first brought into contact with the at least one first capture antibody that specifically binds to a particular epitope under conditions which allow the formation of a first antibody-marker complex. If more than one capture antibody is used, a first multiple capture antibody-marker complex is formed. In a sandwich assay, the antibodies, preferably, the at least one capture antibody, are used in molar excess amounts of the maximum amount of marker expected in the test sample.

Optionally, prior to contacting the test sample with the at least one first capture antibody, the at least one first capture antibody can be bound to a solid support which facilitates the separation of the first antibody-marker complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind the marker. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing the marker is brought into contact with the at least one first capture antibody, the test sample is incubated in order to allow for the formation of a first capture antibody (or multiple antibody)-marker complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the first/multiple capture antibody-marker complex, the complex is then contacted with at least one second detection antibody (under conditions which allow for the formation of a first/multiple antibody-marker second antibody complex). If the first antibody-marker complex is contacted with more than one detection antibody, then a first/multiple capture antibody-marker-multiple antibody detection complex is formed. As with first antibody, when the at least second (and subsequent) antibody is brought into contact with the first antibody-marker complex, a period of incubation under conditions similar to those described above is required for the formation of the first/multiple antibody-marker-second/multiple antibody complex. Preferably, at least one second antibody contains a detectable label. The detectable label can be bound to the at least one second antibody prior to, simultaneously with or after the formation of the first/multiple antibody-marker-second/multiple antibody complex. Any detectable label known in the art can be used.

Kits for Performing the Methods

Provided herein is a kit, which may be used for performing the methods described above. The kit may provide (1) reagents capable of specifically binding to the marker to quantify the levels of the marker, in a biological sample isolated from a subject; (2) a reference standard indicating reference level of the marker, wherein at least one reagent comprises at least one antibody capable of specifically binding the marker; and (3) a reference standard. The kit may further comprise at least one reagent capable of specifically binding (i.e., an antibody) at least one additional biomarker and a reference standard indicating a reference level of the at least one additional biomarker of the condition being assessed, if present.

The kit may comprise the antibodies and a means for administering the antibodies. The kit can further comprise instructions for using the kit and conducting the analysis, monitoring, or treatment.

The kit may also comprise one or more containers, such as vials or bottles, with each container containing a separate reagent. The kit may further comprise written instructions, which may describe how to perform or interpret an analysis, monitoring, treatment, or method described herein.

For example, the kit can comprise instructions for assaying the test sample for one or more biomarkers by immunoassay, e.g., chemiluminescent microparticle immunoassay. The instructions can be in paper form or computer-readable form, such as a disk, CD, DVD, or the like. The antibody can be a detection antibody (meaning an antibody labeled with a detectable label). For example, the kit can contain at least one capture antibody that specifically binds the antigen or biomarker of interest. The kit can also contain a conjugate antibody (such as an antibody labeled with a detectable label) for each capture antibody. Alternatively or additionally, the kit can comprise a calibrator or control, e.g., purified, and optionally lyophilized, and/or at least one container (e.g., tube, microtiter plates or strips, which can be already coated with an anti-biomarker monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying the biomarker of interest.

As alluded to above, any antibodies, which are provided in the kit, such as recombinant antibodies specific for the biomarker, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/ or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a blood sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9- carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution.

If desired, the kit can contain a solid phase, such as a magnetic particle, bead, test tube, microtiter plate, cuvette, membrane, scaffolding molecule, film, filter paper, a quartz crystal, disc or chip. The kit may also include a detectable label that can be or is conjugated to an antibody, such as an antibody functioning as a detection antibody. The detectable label can for example be a direct label, which may be an enzyme, oligonucleotide, nanoparticle, chemiluminophore, fluorophore, fluorescence quencher, chemiluminescence quencher, or biotin. Kits may optionally include any additional reagents needed for detecting the label.

If desired, the kit can further comprise one or more components, alone or in further combination with instructions, for assaying the test sample for another analyte, which can be a biomarker, such as a biomarker of another condition of interest. A sample, such as a serum sample, can also be assayed for an additional biomarker using TOF-MS and an internal standard.

The kit (or components thereof), as well as the method of determining the concentration of the biomarker in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing the biomarker is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, the biomarker, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of biomarker in the sample by means of an embedded algorithm and factory-determined calibration curve.

Subjects

The methods of the present invention may be used on mammalian subjects who are experiencing or are expected to experience a prolonged period of physical inactivity. In certain embodiments, the subject is an adult human subject. As used herein the term "adult human subject" refers to a human subject above age 20. Thus, the adult human subject can be 30, 40, or 50 years of age or more. In certain embodiments the subjects will be elderly, i.e., 50 years of age or greater. The evaluation methods may be used in subjects who are involved in a clinical study where the subjects will experience a prolonged period of inactivity, e.g., the subjects will be in bed for several days, e.g., 10 or more days. The therapeutic and evaluation methods may be used in subjects who are experiencing or are expected to experience prolonged periods of inactivity in a hospital setting, a rehabilitation facility or a private home, etc. For example, the subjects may be subjects who may or will be restricted to bed due to an injury, illness, or surgery. The subjects may also be subjects who self-impose a prolonged period of inactivity, e.g. subjects who are depressed.

Control Values

The difference between the levels of the one or more biomarkers in a biological sample taken from the test subject at 3 or more days of inactivity are compared to a control value. The control value is based on the difference in the levels of the one or more biomarkers in comparable biological samples obtained from a control population, e.g., the general population or a select population of human subjects who have experienced a comparable period of prolonged physical inactivity, e.g., bed rest for 3-10 days or more. For example, the select population may be comprised of male subjects, or female subjects, or elderly subjects, etc. Accordingly, the control values selected may take into account the category into which the test subject falls. Appropriate categories can be selected with no more than routine experimentation by those of ordinary skill in the art.

The difference and, therefore, the control value can take a variety of forms. For example, the control value can be the difference, either negative or positive, in mg/ml, ng/ml, etc. of the circulating levels of the biomarker that is seen untreated control subjects during a similar number of days of inactivity. The control value may be a percent change, either negative or positive, in the circulating levels of the biomarker in untreated control subjects during a comparable period of inactivity.

Control values are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in 7Knapp, R. G., and Miller, M. C. (1992). Clinical Epidemiology and Biostatistics. William and Wilkins, Harual Publishing Co. Malvern, Pa., which is specifically incorporated herein by reference. In addition, reference intervals or expected values for the general population or the select population can be established by following the guidance from the Clinical and Laboratory Standards Institute (CLSI), document C28-A3c (2011).

Interventions

Interventions that may be tested using the present methods include, but are not limited to, nutritional interventions. Examples of such nutritional interventions include, but are not limited to, HMB, high protein diets (e.g., >1 or 1.2 g protein/kg body weight/day), supplements containing high doses of leucine (~15 g/day) or leucine metabolites such as alpha-ketoisocaproate (KIC) and alpha-hydroxyisocaproate (HICA) and high doses of essential amino acids (~45 g/day containing at least 15 g leucine).

Systems for Evaluating the Efficacy of the Intervention

Also provided are systems for determining the efficacy of an intervention on the insulin resistance associated with prolonged physical inactivity in human subjects. In one embodiment the system comprises: (a) a sub-system for identifying a subject undergoing or expected to undergo a prolonged period of physical inactivity in the near future; (b) a sub-system for taking a biological sample from the subject identified in (a) prior to or at the beginning of physical inactivity; (c) a sub-system for administering the intervention to the subject; (d) a sub-system for taking a biological sample from the subject identified in (a) at 3 or more days after the subjects has become physically inactive; (e) a sub-system for measuring the levels of one or more biomarkers selected from the group consisting of C-Peptide, IGFBP-2, and Leptin in the biological samples obtained by sub-systems (b) and (d); and (f) a sub-system for calculating the difference in the levels of the one or more biomarkers in the biological samples obtained by sub-systems (b) and (c). In certain embodiments the system further comprises a sub-system for comparing the differences calculated by sub-system (d) to one or more control values based on the differences in the levels of the one or more biomarkers in comparable biological samples taken from untreated control subjects at the beginning of and following a comparable period of physical inactivity.

In certain embodiments the sub-system for identifying subjects undergoing or expected to undergo a prolonged period of inactivity identifies subjects scheduled to undergo a procedure that typically leads to a period of bed rest of 3 or more days. The sub-system may also identify subjects who have an illness that typically leads to a period of bed rest of 3 or more days. Since elderly subjects typically undergo a longer period of inactivity following surgery, illness, etc., than younger subjects, the system may also comprise a sub-system that identifies the age of the subject. This latter sub-system may be the same as or different from the sub-system that identifies the status of the subject, i.e., if and when the subject may undergo a period of prolonged physical inactivity.

The present systems may be used by facilities housing subjects who are undergoing, who may or, who are expected to undergo a prolonged period of inactivity (e.g., bed rest) for an extended period of time, such as for example, hospitals, rehabilitation centers, nursing homes, etc. All of the sub-systems may be used directly by the facility. Alternatively, some of the sub-systems may be used by testing facilities such as laboratories that report to or are directed to perform certain tests by the facility housing the subject. The present systems may also be used by physicians directing the care of subjects who are undergoing, who may, or who are expected to undergo a prolonged period of inactivity at a hospital, rehabilitation facility, home setting, etc. The present systems may also be used by companies developing interventions directed at reducing the insulin resistance that is associated with prolonged physical inactivity in human subjects.

EXAMPLES

The present methods are based, at least in part, on inventors' discovery that levels of 3 circulating insulin resistance biomarkers increase or decrease by statistically significant amounts in 18 healthy elderly subjects undergoing 10 days of bed rest. The methods are also based, at least in part, on inventors' discovery that intervention with HMB altered the changes in levels of these circulating biomarkers.

Subjects

The following inclusion criteria were verified at screening: male or female ≥60 to ≤79 years of age; body mass index (BMI) ≥20 but ≤35; ambulatory with a Short Performance Physical Battery (SPPB) score of ≥9 (fully functional with no mobility limitations); compliance with prescribed activity level. Exclusion criteria ruled out subjects who had undergone recent major surgery, had active malignancy (exception basal or squamous cell skin carcinoma or carcinoma in situ of the uterine cervix); history of Deep Vein Thrombosis (DVT) or other hypercoagulation disorders; refractory anemia; history of diabetes or fasting blood glucose value >126 mg/dL; presence of partial or full artificial limb; kidney disease or serum creatinine >1.4 mg/dL; evidence of cardiovascular disease assessed during resting or exercise EKG; untreated hypothyroidism; liver disease; chronic or acute GI disease; uncontrolled severe diarrhea, nausea or vomiting; were actively pursuing weight loss; were enrolled in other clinical trials; could not refrain from smoking over the bed rest study period or could not discontinue anticoagulant therapy over bed rest period. Potential subjects were also excluded if they were taking any medications known to affect protein metabolism (e.g., progestational agents, steroids, growth hormone, dronabinol, marijuana, HMB, free amino acid supplements, dietary supplements to aid weight loss).

The 24 healthy subjects initially involved in the study were randomized into two groups. Subjects in the treatment group received two β-hydroxy-β-methylbutyrate (HMB) sachets containing 1.5 grams Ca-HMB (TSI, Salt Lake City, Utah), 4 grams maltodextrin and 200 mg Calcium with additional sweetener and flavoring groups. Subjects in the control group received two control sachets that were identical to the HMB sachets with the exclusion Ca-HMB. This study was a double-blinded study. Neither the investigators nor the subjects were informed of the identity of any of the study products during the clinical portion of the study. Subjects were instructed to consume twice daily by mixing each sachet into a non-caloric, non-caffeinated, non-carbonated, non-milk-based beverage of their choice. Treatment with HMB or Control was initiated 5 days prior to bed rest and was continued until the end of the rehabilitation period.

For diet stabilization over the pre-bed rest and bed rest period, subjects were fed a metabolically controlled diet providing the RDA for protein intake (0.8 g protein/kg body weight per day). Total calorie needs were estimated using the Harris-Benedict equation for resting energy expenditure according to the following equation: For women=[655+(9.56×body weight in kg)+(1.85×height in cm)−(4.68×age in years)]×AF, or, For men=[66+(13.7×body weight in kg)+(5×height in cm)−(6.08×age in years]×AF, where AF=activity factor of 1.6 for the ambulatory and 1.35 for the bed rest periods. Given the total calorie and protein intakes, the remainder of the diet was manipulated to keep the non-protein calories at about 60% from carbohydrates and 40% from fat. Water was provided ad libitum.

After a diet stabilization of 5 days (ambulatory period), subjects remained in bed continuously for 10 days. While confined to bed rest, subjects were allowed to use the bedside commode for urination or were taken in a wheelchair for toileting. Subjects were given the option of taking a sponge bath or showering in a wheelchair. Prophylactic measures were taken to detect and prevent deep vein thrombosis including a blood d-dimer test followed by an ultrasound examination if d-dimer test was positive, passive range of motion exercise during bed rest, the use of TED hose and SCD over the bed rest period. Subjects were offered medication to help mitigate reflux problems associated with being supine. Subjects were constantly monitored by nursing staff and received a daily physical examination by the study physician.

Fasted blood samples were collected from subjects on Day 1 of bed rest and at the end of bed rest for measurement of biomarkers.

Subjects were exited from study if they permanently discontinued product during the pre-bed rest period (Day 1 to Day 5), or if they discontinued product during the bed rest period and had completed less than 8 days of bed rest. Subjects with a positive D-dimer test or ultrasound for deep vein thrombosis (DVT) diagnosis were also exited from the study.

A subject's outcome data were classified as unevaluable for the analysis if one or more of the following events occurred: A. Subject received wrong product, contrary to the randomization scheme, B. Subject received excluded concomitant treatment defined as medications or dietary supplements that affect weight or metabolism (e.g., progestational agents, steroids, growth hormone, dronabinol, marijuana, HMB, free amino acid supplements, dietary supplements to aid weight loss, and fish oil supplements), C. subject had <67% of total study product consumption at Final Visit/Exit as determined by product consumption records.

The final analytic sample size is n=18 subjects, n=8 in the control group (n=1 male, n=7 female) and n=10 (n=2 male, n=8 female) in the experimental HMB group.

Biomarker Analysis

Rules Based Medicine (RBM, Myriad, Tex.) data generated from the RBM Human Discovery map v1.0 consists of n=187 biomarkers measured in serum collected at two time points, pre-bed rest and post-bed rest from 18 elderly subjects. The distribution of each marker was evaluated. Each marker has a least detectable dose (LDD) value, defined as the mean+3 standard deviations (SD) of 20 blank samples. For any subject whose marker result was ≤LDD, the LDD value as provided by RBM was imputed. If the marker result was >LDD, the original result was used. Any marker in which ≥30% of all subject's results were imputed was excluded from further statistical analyses. Of the initial n=187 RBM markers (addendum 1), n=63 markers (Addendum 2) from the RBM dataset were excluded from further analyses, leaving n=124 markers for evaluation.

Statistical Evaluation

Changes in RBM Biomarkers

The control group was examined to see which insulin resistance biomarkers changed over bed rest. Individual univariate dependent t-tests were performed on each of the 124 markers. There were a total of 8 participants who had matched data over bed rest within the control group. From the initial univariate analysis, 3 insulin resistance markers showed a statistically significant change over bed rest, with an unadjusted p-value less than 0.05.

Significance of ANCOVA tests

In order to assess the changes in the markers over bed rest that may be mediated by HMB intervention, individual univariate ANCOVA analyses were subsequently performed on each of the 3 (unadjusted) significant insulin resistance markers from the multiple dependent t-tests. Using a Bonferonni adjusted p-value of 0.0038 (0.05/13), three insulin resistance markers were significant. This result indicates that these 3 insulin resistance markers showed a statistical difference after bed rest between the control and HMB groups while controlling for existing differences at baseline (pre-bed rest).

Example 1

Effect of Hmb Intervention on Circulating Levels of Igfbp-2 in Subjects who have Experienced 10 Days of Bedrest IGF-binding proteins prolong the half-life of the IGFs and alter the interaction of IGFs with their cell surface receptors. A decrease in circulating IGFBP-2 is associated with an increase in insulin resistance in human subjects.

As shown in Table 1, there was an average decrease of −30.54 ng/ml or a −24.56% decrease in circulating levels of IGFBP-2 in 8 control subjects after 10 days of bed rest. In contrast, the average decrease in IGFBP-2 levels in blood from 10 subjects treated with HMB was much less. As shown in Table 1, there was an average decrease of −20.89 ng/ml or a −15.63% decrease in blood levels of IGFBP-2 in these HMB treated subjects. These results show that HMB reduces or attenuates the decrease in blood levels of IGFBP-2 that occurs in control subjects during prolonged bed rest.

Example 2

Effect of Hmb Intervention on Circulating Levels of C-Peptide in Subjects who have Experienced 10 Days of Bedrest C-peptide (Swiss-Prot Accession Number: P01308) is produced by the beta cells of the pancreas as part of the proinsulin molecule (insulin precursor). An increase in circulating C-peptide is associated with insulin resistance in human subjects.

As shown in Table 1, there was an average increase of 0.54 ng/ml or an average increase of 43.0% in circulating levels of C-peptide in 8 control subjects after 10 days of bed rest. In contrast, the average increase in C-peptide levels in blood from 10 HMB treated subjects was much less. As shown in Table 1, there was an average increase of 0.28 ng/ml or an increase of 29.59% in blood levels of C-peptide in these HMB treated subjects after 10 days of bed rest. These results show that HMB reduces or attenuates the increase in blood levels of C-peptide that occurs in untreated control subjects during prolonged bed rest.

Example 3

Effect of Hmb Intervention on Circulating Levels of Leptin in Subjects who have Experienced 10 Days of Bedrest Leptin is a 16-kDa adipocyte-derived hormone that circulates in the serum in the free and bound form. (Mantzoros C S, *Ann Intern Med* 1999; 130:671-680. Studies have shown that insulin resistance is associated with elevated plasma Leptin levels independent of body fat mass. (Segal K R, et al., *Diabetes* 1996; 45:988-991.)

As shown in Table 1, there was an average increase of 5.06 ng/ml in circulating levels of Leptin in 8 control subjects after 10 days of bed rest. In contrast, there was a lower average increase of 4.11 ng/ml in circulating levels of Leptin in 10 HMB treated subjects after 10 days of bed rest. These values are significantly lower than the control values. These results show that HMB reduces or attenuates the increase in blood levels of Leptin that occurs in untreated control subjects during prolonged bed rest.

CONCLUSION

Taken together, all 3 markers indicate a protective effect of HMB against development of insulin resistance during prolonged physical inactivity in a human subject.

TABLE 1

Insulin Resistance Markers That Change With HMB Treatment Over Bed Rest

| Biomarkers | Pre-bed rest Mean (ng/ml) | Stdev | Post-bed rest Mean (ng/ml) | Stdev | Change (ng/ml) |
|---|---|---|---|---|---|
| | Control (n = 8) | | | | |
| Leptin | 18.30 | 10.57 | 23.36 | 10.76 | 5.06 ± 1.88 |
| C-peptide | 1.25 | 0.71 | 1.78 | 1.22 | 0.54 ± 0.22 |
| Insulin-like Growth Factor-Binding Protein 2 (IGFBP-2) | 102.88 | 44.29 | 72.34 | 26.18 | −30.54 ± 13.64 |
| | HMB Treatment (n = 10) | | | | |
| Leptin | 15.20 | 5.39 | 19.31 | 4.95 | 4.11 ± 1.89 |
| C-peptide | 1.41 | 0.33 | 1.69 | 0.30 | 0.28 ± 0.08 |
| Insulin-like Growth Factor-Binding Protein 2 (IGFBP-2) | 127.86 | 17.02 | 106.97 | 15.15 | −20.89 ± 6.84 |

*treatment difference, univariate ANCOVA p value <0.0001)

What is claimed is:

1. A method of reducing the effect of prolonged physical inactivity on insulin resistance in a subject who is experiencing ten or more days of physical inactivity, the method comprising:
   administering a therapeutically effective amount of β-hydroxy-β-methylbutyric acid (HMB) or a salt thereof to the subject, wherein the subject is from 60 to 79 years of age and does not have diabetes or a fasting blood glucose value greater than 126 mg/dL.

2. The method of claim 1, wherein HMB is administered in an amount, manner, and for a time sufficient to lessen the increase in circulating levels of C-peptide, the decrease in circulating levels of IGFBP-2, and/or the increase in circulating levels of Leptin that occurs with prolonged physical inactivity in untreated control subjects.

3. The method of claim 1, wherein HMB is administered in an amount, manner, and for a time sufficient to reduce the increase in circulating levels of C-peptide that occurs with prolonged physical inactivity in untreated control subjects.

4. The method of claim 1, wherein HMB is administered in an amount, manner and for a time sufficient to reduce the increase in circulating levels of Leptin that occurs with prolonged physical inactivity in untreated control subjects.

5. The method of claim 1, wherein HMB is administered in an amount, manner and for a time sufficient to attenuate the decrease in circulating levels of IGFBP-2 that occurs with prolonged physical inactivity in untreated control subjects.

6. The method of claim 1, wherein HMB is administered in an amount, manner and for a time sufficient to keep the levels of C-peptide and/or IGFBP-2 in biological samples taken from the subject following 3 or more days of physical inactivity comparable to the baseline levels of C-peptide and/or IGFBP-2 in a biological sample taken from the subject at the beginning of or prior to the physical inactivity.

7. A method for reducing insulin resistance due to prolonged physical inactivity, the method comprising:
   identifying a subject as undergoing prolonged physical inactivity of ten or more days; and
   administering β-hydroxy-β-methylbtyric acid (HMB) or a salt thereof to the identified subject during the days of prolonged physical inactivity at a level effective to reduce the insulin resistance; and wherein the subject is from 60 to 79 years of age and does not have diabetes or a fasting blood glucose value greater than 126 mg/dL.

8. The method of claim 7 wherein the prolonged physical inactivity comprises bed rest or immobilization.

9. The method of claim 7 wherein the subject is administered at least two grains per day of the HMB or the salt thereof.

10. The method of claim 7 wherein the subject is administered from 20 to 40 mg/kg body weight per day of the HMB or the salt thereof.

11. The method of claim 7 wherein the step of administering comprises the administration of the salt, and wherein the salt is selected from the group consisting of a sodium salt, a potassium salt, a magnesium salt, a chromium salt, and a calcium salt.

12. The method of claim 7 further comprising administering the HMB or the salt thereof to the subject after the physical inactivity ends.

13. A method for reducing insulin resistance due to prolonged physical inactivity, the method comprising:
 identifying a subject who is experiencing ten or more days of physical inactivity; and
 administering β-hydroxy-β-methylbutyric acid (HMB) or a salt thereof to the identified subject to reduce the insulin resistance: and wherein the subject s from 60 to 79 years of age and does not have diabetes or a fasting blood glucose value greater than 126 mg/L.

14. The method of claim 13 wherein the step of identifying comprises determining that the subject is scheduled to undergo a surgery within the next month.

15. The method of claim 13 further comprising identifying the subject as greater than fifty years of age prior the step of HMB administration.

* * * * *

UNITED STATES PATENT AND TRADEMARK OFFICE
CERTIFICATE OF CORRECTION

PATENT NO.         : 9,713,598 B2                                       Page 1 of 1
APPLICATION NO.    : 14/775972
DATED              : July 25, 2017
INVENTOR(S)        : Luo et al.

It is certified that error appears in the above-identified patent and that said Letters Patent is hereby corrected as shown below:

Claim 9, Column 23, Line 2, change "grains" to --grams--.

Claim 13, Column 23, Line 21, change "s" to --is--.

Signed and Sealed this
Twenty-sixth Day of September, 2017

Joseph Matal
*Performing the Functions and Duties of the
Under Secretary of Commerce for Intellectual Property and
Director of the United States Patent and Trademark Office*